United States Patent
Wieser et al.

(10) Patent No.: US 6,248,881 B1
(45) Date of Patent: *Jun. 19, 2001

(54) INTERMEDIATES AND PROCESS FOR THE PRODUCTION OF 3-VINYL CEPHALOSPORINS

(75) Inventors: Josef Wieser, Kufstein; Gerd Ascher, Kundl; Johannes Ludescher, Breitenbach; Herbert Sturm, Innsbruck, all of (AT)

(73) Assignee: Biochemie GmbH, Kundl (AT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/829,572

(22) Filed: Mar. 31, 1997

Related U.S. Application Data

(63) Continuation of application No. 08/149,431, filed on Nov. 9, 1993, now abandoned, which is a continuation-in-part of application No. 08/069,239, filed on May 28, 1993, now Pat. No. 5,401,841, said application No. 08/069,239, filed on May 28, 1993, now Pat. No. 5,401,841, is a continuation of application No. 07/848,457, filed on Mar. 9, 1992, now abandoned.

(30) Foreign Application Priority Data

| Mar. 8, 1991 | (AT) | 504/91 |
| May 17, 1991 | (AT) | 1018/91 |
| Nov. 10, 1992 | (AT) | 2212/92 |

(51) Int. Cl.$^7$ .................. C07D 501/22; C07D 501/24; C07D 501/04
(52) U.S. Cl. .................. 540/215; 540/222
(58) Field of Search .................. 540/215, 222

(56) References Cited

U.S. PATENT DOCUMENTS

| 4,110,534 | * 8/1978 | Clark et al. | 544/16 |
| 4,406,899 | 9/1983 | Aburaki et al. | 424/246 |
| 4,504,657 | 3/1985 | Bouzard et al. | 544/30 |
| 4,699,979 | 10/1987 | Hoshi et al. | 540/215 |
| 4,703,118 | 10/1987 | Lord et al. | 540/224 |
| 4,705,851 | * 11/1987 | Takaya et al. | 544/16 |
| 5,132,419 | 7/1992 | Lanz et al. | 540/215 |
| 5,171,854 | 12/1992 | Schmidt et al. | 540/222 |
| 5,401,841 | * 3/1995 | Ascher et al. | 540/215 |
| 5,856,474 | * 1/1999 | Ascher | 540/222 |

FOREIGN PATENT DOCUMENTS

| 0382875 | 4/1987 | (AT) . |
| 2103014 | 7/1971 | (DE) . |
| 3516777 | 10/1985 | (DE) . |
| 0103264 | 3/1984 | (EP) . |
| 0122002 | 10/1984 | (EP) . |
| 0292808 | 11/1988 | (EP) . |
| 0299587 | 1/1989 | (EP) . |
| 0335390 | * 10/1989 | (EP) . |
| 0503453 | * 9/1992 | (EP) . |
| 0503493 | 9/1992 | (EP) . |
| 2152497 | 8/1985 | (GB) . |
| 2159515A | 12/1985 | (GB) . |

OTHER PUBLICATIONS

Chim. Pharm. Bull. 36(7), 2354 (1988).
Tetrahedron Letters 23(21), 2187 (1982).
Derwent No. 50795(S) Jul. 29, 1971 (Abstracting Patent No. DT–2103014).
Carruthers, Campridge Texts in Chemistry and Biochemistry, Cambridge University Press. Third Edition, Some Modern Methods of Organic Synthesis, pp. 124–139, 1986.

* cited by examiner

*Primary Examiner*—Mark L Berch
(74) *Attorney, Agent, or Firm*—Susan Hess

(57) ABSTRACT

A process for the production of a 3-vinylcephalosporin compound of formula I

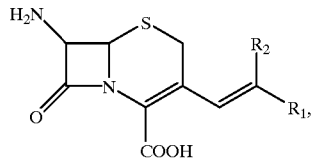

wherein $R_1$ and $R_2$ may be the same or different and denote hydrogen or an organic radical, which comprises subjecting a 3-iodomethyl-cephalosporin to a Wittig reaction in the presence of a weak base.

3 Claims, No Drawings

INTERMEDIATES AND PROCESS FOR THE PRODUCTION OF 3-VINYL CEPHALOSPORINS

This is a continuation of application Ser. No. 08/149,431, filed Nov. 9, 1993, ABN which in turn is a continuation-in-part of application Ser. No. 08/069,239, filed May 28, 1993, which issued as U.S. Pat. No. 5,401,841 on Mar. 28, 1995, said application Ser. No. 08/069 239 being a continuation of application Ser. No. 07/848,457, filed Mar. 9, 1992, now abandoned.

The invention relates to an economical and simple process for the production of 3-vinylcephalosporin compounds of formula I

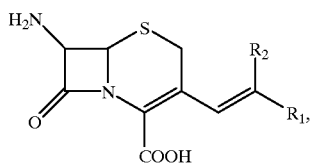

wherein $R_1$ and $R_2$ may be the same or different and denote hydrogen or an organic radical.

The compounds of formula I are known to be useful starting products for the production of valuable 3-substituted vinyl cephalosporins.

In substituents $R_1$ and $R_2$, the organic radical may signify for example an optionally branched alkyl, alkenyl or aikinyl group; a totally or partially saturated cycloalkyl radical; or an optionally substituted aryl radical, aralkyl radical or heterocycle. The cycloalkyl radical, aryl radical, aralkyl radical or heterocycle may be substituted in any position, for example by halogen, nitrogen, sulphur, alkoxy, aryloxy, or a functional group such as a carbalkoxy or carboxamido group. $R_1$ and $R_2$ may also form part of an optionally substituted ring system.

In a preferred embodiment of the invention one of $R_1$ and $R_2$ is hydrogen and the other is:

i) hydrogen, lower alkyl, lower alkenyl, or lower alKinyl;
ii) lower cycloalkyl, lower cycloalkyl lower alkyl, aryl, (aryl)-lower alkyl, a heterocyclic group or a heterocyclyl-(lower)-alkyl, the ring of each of which may be optionally substituted by 1 to 3 lower alkoxy, lower alkylthio, halogen, lower alkyl, nitro, hydroxy, acyloxy, carboxy, carbalkoxy, lower alkylcarbonyl, lower alkylsulfonyl, lower alkoxysulfonyl, amino-(lower)-alkyl amino or acylamido groups; or
iii) a group of formula —$CH_2Z$, in which Z is a) hydroxy, lower alkoxy, formyloxy, acetyloxy, lower alkylsulfonyloxy, halogen, N-mono(lower)alkylcarbamoyloxy, or N,N-di(lower)alkylcarbamoyloxy; b) a heterocyclic group; c) a group of formula —$S(O)_mR_9$ in which $R_9$ is an aliphatic, araliphatic, alicyclic, aromatic or heterocyclic group, and m is 0, 1 or 2; or d) an acyclic or cyclic ammonium group.

Suitable heterocyclic groups include single or fused heterocyclic rings having 4 to 7, preferably 5- or 6- atoms in each ring. Each ring has up to four hetero atoms in it selected from oxygen, nitrogen and sulphur. Also each heterocyclic ring may have 1 to 3 optional substituents selected from ($C_{1-4}$) alkyl, ($C_{1-4}$) alkoxy, halogen, trihalo-($C_{1-4}$) alkyl, hydroxy, o)o, mercapto, amino, carboxyl, carbamoyl, di-($C_{1-4}$) alkylamino, carboxymethyl, carbamoylmethyl, sulfomethyl and methoxycarbonylamino.

Examples of suitable heterocycle rings include unsubstituted and substituted imidazolyl, diazolyl, triazolyl, tetrazolyl, thiazolyl, thiadiazolyl, thiatriazolyl, oxazolyl, oxadiazolyl, benzimidazolyl, benzoxazolyl, benzothiazolyl, triazolylpyridyl, purinyl, pyridyl, pyrimidinyl, pyridazinyl, pyrazolyl and triazinyl.

Preferably, suitable heterocycle rings include unsubstituted and substituted 5-hydroxy-4-pyridon-2-yl, 1,2,3-triazolyl; 1,2,4-triazolyl; tetrazolyl; oxazolyl; thiazolyl; 1,3,4-oxadiazolyl; 1,3,4-thiadiazolyl or 1,2,3-thiadiazolyl. Preferably the heterocycle is 1,5-dihydroxy-4-pyridon-2-yl, 5-hydroxy-1-methyl-4-pyridon-2-yl, 5-hydroxy-4-pyridon-2-yl, 1-methyl-1H-tetrazol-5-yl-2-methyl-1,3,4-thiadiazol-5-yl, 1-carboxymethyl- 1H-tetrazol-5-yl, 6-hydroxy-2-methyl-5-oxo-2H-1,2,4-triazin-3-yl, 1,2,3-triazol-5-yl, and 4-methyl-thiazol-5-yl.

Examples of acyclic ammonium groups include (1-carbamoyl-2--hydroxyethyl)-dimethylammonium, (carbamoylmethyl)(ethyl)-methylammonium or trimethyl ammonium.

Examples of cyclic ammonium groups are pyrrolidinium, which is N-substituted by alkyl, carbamoylalkyl, aminoalkyl or carboxyalkyl; pyridinium or cyclopentenopyridinium, which may be mono- or di-substituted by alkyl, halogen, hydroxy, carboxamido, alkoxycarbonyl, amino, monoalkylamino or dialkylamino.

Except where otherwise indicated, the organic radicals preferably contain up to 10 carbon atoms and "lower" means the group has up to 4 carbon atoms.

Processes for the production of compounds of formula I are known and are discussed in EP 0503453, the disclosure of which is incorporated by reference. However, as discussed in EP 0503453, these known processes require the use of expensive protection groups and require a multiplicity of intermediate stages. The invention disclosed in EP 0503453 addressed the problems of the prior art by making use of silyl protection groups in a Wittig reaction using 7-amino cephalosporanic acid as starting reagent.

The process disclosed in EP 0503453 proceeds according to the following reaction scheme:

i) a compound of the formula II

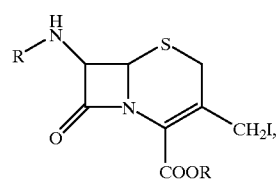

in which R is a silyl protecting group, is reacted with a compound of the formula $P(R_4)_3$ or $P(OR_4)_3$ to produce a compound of formula III

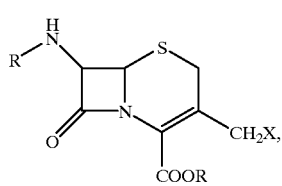

in which X is —$P(R_4)_3.I$ or —$P(O).(OR_4)_2$, R is as defined above and $R_4$ is a lower alkyl groupl or an aryl group;

ii) the compound of the formula III is then reacted with a strong base to produce a compound of the formula IV

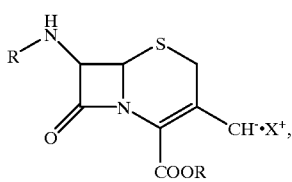

IV in which $X^+$ is $-P(O).(OR_4)_2.Y$, $R_4$ and $R$ are as defined above and $Y$ is a cation of the alkali series or the protonated form of a strong organic base; and iii) the compound of the formula IV is reacted with a compound of the formula V

V in which $R_1$ and $R_2$ are as defined above, to produce the compound of the formula I. The resulting process is simple, economical and may be carried out in a single reaction vessel. Also, it has the advantage that the silyl protection groups are removable by simple hydrolysis, or alcoholysis.

The base used in step ii) is a strong organic base and guanidines (for example tetramethylguanidine), amidines (for example 1,8-diazabicyclo[5.4.0]undec-7-ene and 1,5-diazabicylo[4.3.0]non-5-ene), alkali salts of nitrogen-containing compounds (for example the Li or Na salts of 1,1,1,3,3,3-hexamethyldisilazane and Li-diisopropylamide), butyllithium, hydrides of alkali metals, and iminophosphoranes are given as suitable examples. It is also mentioned that the bases should be free of moisture and should not contain any parts that could be silylated, so as to maintain the degree of silylation of the product.

It has now been surprisingly found that the process described in EP 0503453 may be carried out using weaker bases. This is of particular advantage since the reaction may be carried out under milder conditions.

Therefore this invention provides a process, substantially as defined above, for the production of a compound of formula I which is improved by the use of a weak base in step ii).

That a weaker base could be used in a Wittig reaction is indeed surprising. The use of the weaker base has the advantage that the possibility of opening the β-lactam ring is reduced and superfluous condensation of the base with the aldehyde or ketone is avoided or restricted.

Preferably the weak base is such that its conjugate acid has a silylatable function and the reaction step ii) is carried out in the presence of a silylating agent to cause silylation of the silylatable function. Surprisingly, the reaction proceeds without the silyl protecting group on the 7-amino group, which is a very potent silylating agent and which is easily removed, being removed by the base or conjugate acid. If the silyl protecting group were to be removed during the reaction, the amino group would be free to react with the aldehyde or ketone of formula V and this would cause the reaction to collapse.

Preferably the weak base is selected from:
i) compounds that have the formula

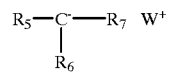

in which $R_5$ is hydrogen, alkyl or aryl; $R_6$ and $R_7$, which may be the same or different, are each an activated group of the formula $-COOR_8$, $-CN$, $-SO_2R_8$, $-COR_8$, or $-CON(R_8)_2$; or $R_5$ and $R_6$, which may be the same or different, are each aryl and $R_7$ is an activated group of the formula $-COOR_8$, $-CN$, $-SO_2R_8$, $-COR_8$ or $-CON(R_8)_2$; $W^+$ is a cation (for example lithium, sodium, or calcium); and $R_8$ is alkyl, cycloalkyl or aryl; and ii) salts of carboxylic acids of the formula $R_{10}$, $-COO^-$ $W^+$ in which $R_{10}$ is an optionally branched alkyl group or an optionally substituted aryl group; and $W^+$ is as defined above.

Particularly preferred weak bases are lithium and sodium salts of malonic acid diethyl esters, acetoacetic acid esters, acetic acid, pivalic acid, or ethylhexanoic acids, or lithium sales of benzoic acids.

The silylating agent may be added to the reaction mixture prior to the addition of the weak base or simultaneously with the weak base; in both cases to cause the silylation of silylatable function of the conjugate acid of the weak base. N,O-bis(trimethylsilyl)-acetamide and bissilylurea are particularly suitable as silylating agents and further examples are given in EP 0503453.

The reaction may be carried in a suitable solvent or solvent mixture which is inert under the reaction conditions, for example an inert ether (such as tetra-hydrofuran, diethyl ether, an ethylene glycol dialkyl ether or a tert.butylmethyl ether), an inert amide (such as dimethylformamide, dimethylacetamide or N-methylpyrrolidone), an urea (such as tetra-methylurea, 1,3-dimethyl-3,4,5,6-tetrahydro-2(1H)-pyrimidone, or 1,3,2-imidazolidinonee a nitrile (such as acetonitrile), or a halogenated hydrocarbon (such as dichloromethane).

Should a substituent of the aldehyde or the ketone of formula V contain a function which is easily silylated, this should be blocked temporarily with an appropriate silylation agent prior to the reaction. The amount of the compound of formula V may be stoichiometrical or in excess based on the amount of the compound of formula IV.

The reaction may be carried out over a wide temperature range, preferably at a temperature of between −70° C. and +70° C.

The compounds of formula I may be isolated in a conventional manner. The silyl protecting groups may be removed by simple hydrolysis or alcoholysis. This may be done either by adding the desilylation agent to the reaction mixture, or by extracting the product into a separable aqueous phase, adding water (under alkaline or acidic conditions) and precipitating by adjusting the pH value to the isoelectric point, optionally adding an organic solvent.

The compounds of formula II are known and may be produced as described in EP 0503453.

The compounds of formula I are important starting materials for the production of valuable cephalosporin antibiotics. Cephalosporins which are vinyl-substituted in 3-position are either resorbed orally, or when administered parenterally, are characterized for their very broad, efficient spectrum of activity. The following compounds may be produced for example:

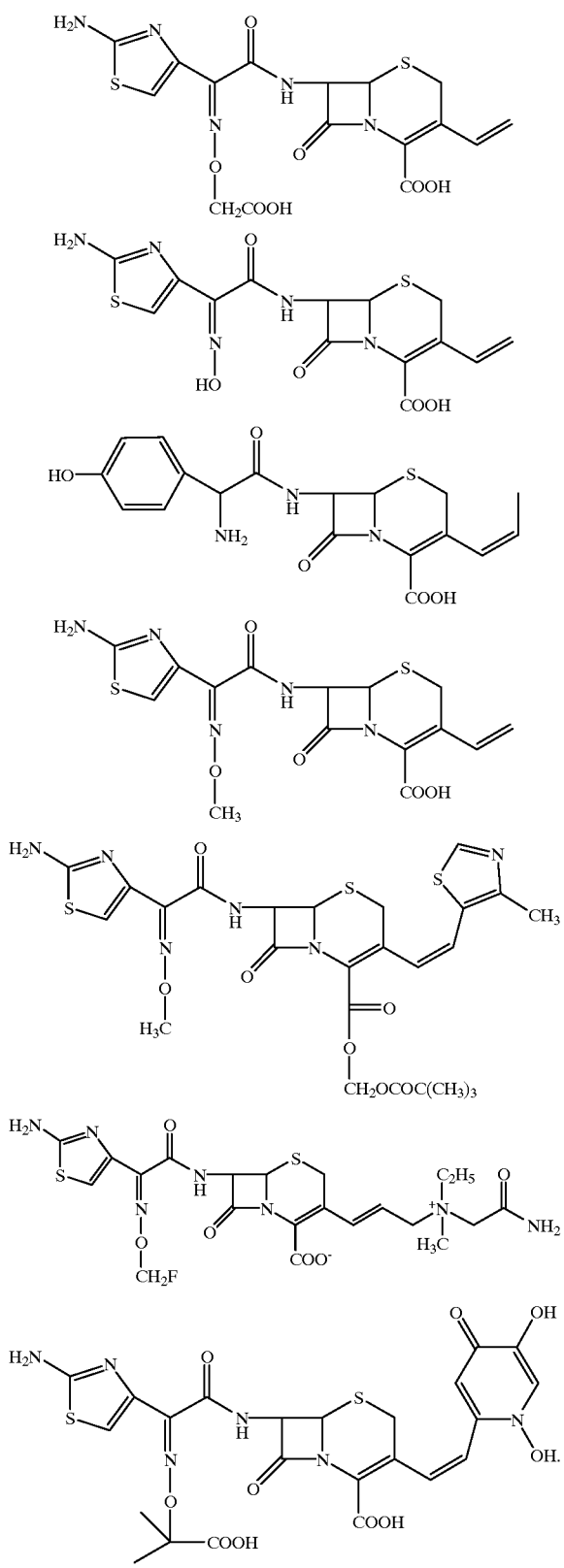

In the following examples, which illustrate the invention more fully, but in no way limit its scope, all temperatures are given in degrees celsius.

EXAMPLE 1

7-Amino-3-(3-acetoxy-1-propenyl)-3-cephem-4-carboxylic acid 7.5 ml of N,O-bis(trimethylsilyl)acetamide is added to 25 ml of a dichloromethane solution containing 6 g of 7-trimethylsilylamino-3-triphenyl-phosphoniummethyl-3-cephem-4-carboxylic acid trimethylsilylester-iodide on ice. 25 ml of a N-Methylpyrrolidone solution, at 5 to 10°, containing 2.35 g sodium aceto-acetic acid ethyl ester, is added dropwise. The dark red solution is then cooled to 2° and 5:16 g acetoxyaldehyde is added dropwise. The reaction mixture is then stirred for 2 hours at 100 and then added to a mixture of 100 ml acetic acid and 100 ml water. The pH of the aqueous phase is adjusted to 7 with ammonia and the organic phase is separated off. The pH is adjusted to 3.5 by adding 1:1 diluted concentrated HCl, whereupon the title compound precipitates. The suspension is stirred for 30 minutes at 50°, the title compound is filtered off, washed in acetone and dried.

EXAMPLE 2

7-Amino-3-(prop-1-enyl)-3-cephem-4-carboxylic acid 5 ml of N,O-bis(trimethylsilyl)acetamnide is added to 25 ml of a dichloromethane solution containing 6 g of 7-trimethylsilylamino-3-triphenyl-phosphoniummethyl-3-cephem-4-carboxylic acid trimethylsilylester-iodide on ice. 25 ml of a N-Methylpyrrolidone solution, at 5 to 10°, containing 2.35 g sodium malonic acid diethyl ester, is added dropwise. Thereafter the solution is cooled to −10° and 1.32 g acetaldehyde, dissolved in 10 ml dichloromethane, is added. After the addition of the acetaldehyde, the reaction mixture is stirred for 48 hours at 0°. Thereafter the process proceeds as described in example 1.

EXAMPLE 3

7-Amino-3-(prop-1-enyl)-3-cephem-4-carboxylic acid 36.5 ml of N,O-bis(trimethylsilyl)acetamide is added to 500 ml of a dichloromethane solution containing 24 g of 7-trimethylsilylamino-3- triphenyl-phosphoniummethyl-3-cephem-4-carboxylic acid trimethylsilylester-iodide at a temperature of −10°. A suspension of 12.8 g lithium benzoate in 75 ml N-Methylpyrrolidone is added. 9 g of acetaldehyde is added and the reaction mixture is stirred for 2 days at 0°. Superfluous acetaldehyde and most of the dichloromethane are removed in a rotary evaporator. The residue is then stirred in 1500 ml of water and then filtered. The residue is dissolved in 200 ml aqueous ammonia and the aqueous phase is extracted twice using 100 ml dichloromethane. After removal of the organic phase, 1:1 diluted concentrated HCI is added to the aqueous phase to bring the pH to 3.5 whereupon the title compound precipitates. The suspension is stirred for 30 minutes at 5°, the tide compound is filtered off, washed in acetone and dried.

EXAMPLE 4

7-Amino-3-(3-acetoxy-1-propen-1-yl)-3-cephem-4-carboxylic acid 7.5 ml of N,O-bis(trimethylsilyl)acetamide is added to 25 ml of a dichloromethane solution containing 6 g of 7-trimethylsilylamino-3-triphenyl-phosphoniummethyl-3-cephem-4-carboxylic acid trimethylsilylester-iodide on ice. 15 ml of a N-methylpyrrilidone solution containing 2.5 g sodium-ethylhexanoate is added dropwise at 0 to 5°. 5 ml of acetoxy-acetaldehyde is added dropwise. The reaction mixture is stirred overnight at 0° and then processed as described in example 1.

EXAMPLE 5

7-Amino-3-[2-(4-methyl-5-thiazolyl)vinyl]-3-cephem-4-carboxylic acid 25 g of a dichloromethane solution containing 10.2 g of 7-trimethylsilylamino-3-triphenyl-phosphoniummethyl-3-cephem-4-carboxylic acid trimethylsilylester-iodide is cooled to a temperature of −10°. 4.7 ml of N,O-bis (trimethylsilyl)acetamide, 11 ml dimethylformamide and 1.1 g lithium acetate are added and the mixture stirred at 0 to 5° for 30 minutes. A solution of 2 g of 4-methyl-thiazol-5-carboxyaldehyde in 5 ml dichloromethane is then added dropwise. The mixture is then stirred for 10 hours at 30°, cooled to 10° and stirred for a further hour at 10°. The tide compound is separated using a suction filter, washed with methanol and vacuum dried.

EXAMPLE 6

7-Amino-3-(prop-1-enyl)-3-cephem-4-carboxylic acid 220.7 g of a dichloromethane solution containing 68.7 g of 7-trimethylsilylamino-3-triphenyl-phosphoniummethyl-3-cephem-4-carboxylic acid trimethylsilylester-iodide is cooled to a temperature of −10°. 58.4 ml of N,O-bis (trimethylsilyl)acetamide and 81 ml N,N-dimethylacetamide is added while stirring. A solution of 14.05 g lithium pivalate is added and the mixture stirred for 30 minutes at −10°. 17.2 ml of acetaldehyde is added and the reaction mixture is stirred for 90 minutes at −10° and then overnight at 0°. Superfluous acetaldehyde and some of the dichloromethane are removed in a rotary evaporator under vacuum and at 20°. The residue is then stirred into 500 ml of ice-cold water and 100 ml dichloromethane. The pH value is adjusted to 8.5 with aqueous ammonia. The phases are then separated and the aqueous phase is washed with 100 ml dichloromethane and combined with 200 ml acetone. The pH is adjusted to 3.5 with 1:1 diluted concentrated hydrochloric acid at 30° to precipitate the title compound. The suspension is held in the ice bath for 2 hours whilst stirring, and the title compound is isolated using a suction filter. The title compound is washed with a mixture of 100 ml of water and 50 ml acetone and then again with 50 ml of acetone. The title compound is then dried in a vacuum drying chamber at 40°.

What is claimed is:

1. A compound of formula

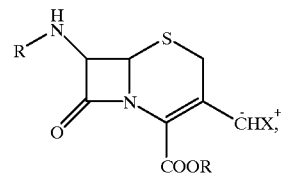

IV wherein
$X^+$ is $—P(R_4)_3$ or $—P(O)(OR_4)_2 \, Y^+$,
$R_4$ is a $(C_{1-4})$alkyl group or an aryl group containing up to 10 carbon atoms,
R is a silyl protecting group, and
Y is an alkali metal cation.

2. A compound of formula

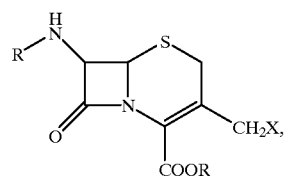

III wherein
R is a silyl protecting group,
X is $—P(R_4)_3$ I or $—P(O)(OR_4)_2$, and
$R_4$ is a $(C_{1-4})$alkyl group or an aryl group containing up to 10 carbon atoms.

3. The compound of claim 2 which is 7-trimethylsilyl-amino-3-triphenylphosphoniummethyl-3-cephem-4-carboxylic acid trimethylsilylester-iodide.

* * * * *

UNITED STATES PATENT AND TRADEMARK OFFICE
CERTIFICATE OF CORRECTION

PATENT NO. : 6,248,881 B1  
DATED : June 19, 2001  
INVENTOR(S) : Wieser et al.

Page 1 of 1

It is certified that error appears in the above-identified patent and that said Letters Patent is hereby corrected as shown below:

<u>Column 8,</u>  
Line 21 should read -- $X^+$ is $- P^+(R_4)_3$ or $-P(O)(OR_4)_2\ Y^+$, --

Signed and Sealed this

Fourteenth Day of May, 2002

Attest:

JAMES E. ROGAN  
*Attesting Officer*  *Director of the United States Patent and Trademark Office*